US012702777B2

(12) United States Patent
Rafiqpoor

(10) Patent No.: US 12,702,777 B2
(45) Date of Patent: Aug. 11, 2026

(54) VENTILATION ASSEMBLY AND HARNESS

(71) Applicant: LMA OPTIMIZER B.V., Amsterdam (NL)

(72) Inventor: Khaled Rafiqpoor, Roermond (NL)

(73) Assignee: LMA OPTIMIZER B.V., Amsterdam (NL)

(*) Notice: Subject to any disclaimer, the term of this patent is extended or adjusted under 35 U.S.C. 154(b) by 966 days.

(21) Appl. No.: 17/642,063

(22) PCT Filed: Sep. 14, 2020

(86) PCT No.: PCT/NL2020/050567
§ 371 (c)(1),
(2) Date: Mar. 10, 2022

(87) PCT Pub. No.: WO2021/049941
PCT Pub. Date: Mar. 18, 2021

(65) Prior Publication Data

US 2024/0058559 A1 Feb. 22, 2024

(30) Foreign Application Priority Data

Sep. 13, 2019 (NL) ...................................... 2023830

(51) Int. Cl.
*A61M 16/04* (2006.01)
*A61M 16/06* (2006.01)

(52) U.S. Cl.
CPC .... *A61M 16/0409* (2014.02); *A61M 16/0694* (2014.02)

(58) Field of Classification Search
CPC .............. A61M 16/04; A61M 16/0402; A61M 16/0409; A61M 16/0683; A61M 16/0688;
(Continued)

(56) References Cited

U.S. PATENT DOCUMENTS 5,249,571 A * 10/1993 Brain ................ A61M 16/0409 128/207.14
6,016,807 A * 1/2000 Lodge ..................... A61F 13/12 128/848
(Continued)

FOREIGN PATENT DOCUMENTS

CN 103357096 A 10/2013
DE 102005025996 * 6/2005 ............ A61M 16/04
(Continued)

OTHER PUBLICATIONS

First Examination Report for corresponding Chinese application No. 202080064731.6; dated Aug. 7, 2024 (12 pages) Machine Translation.

(Continued)

*Primary Examiner* — Victoria Murphy
*Assistant Examiner* — Sydney Reyes Russell
(74) *Attorney, Agent, or Firm* — Mendelsohn Dunleavy, PC; Kevin J. Dunleavy

(57) ABSTRACT

A ventilation assembly (37) for use in ventilation of a subject using a laryngeal mask (5) comprises a head-wearable harness (39) and a pusher (41). The harness is arrangeable on the subject's head (H) for supporting the pusher against the floor of the mouth (15) of the subject (P). The pusher is arranged to displace soft tissue of the floor of the mouth in cranial direction relative to the mandible (29) of the subject for, when the laryngeal mask is installed in the airway of the subject, urging internal soft tissue of the subject against the laryngeal mask in the airway of the subject. A harness for such assembly is also disclosed.

20 Claims, 12 Drawing Sheets

(58) Field of Classification Search
CPC ....... A61M 16/0694; A61F 5/56; A61F 5/012; A61F 5/055; A61F 13/12
See application file for complete search history.

(56) References Cited

U.S. PATENT DOCUMENTS

| | | | | |
|---|---|---|---|---|
| 7,047,977 | B2 | 5/2006 | Frank | |
| 7,124,758 | B1 | 10/2006 | Frank | |
| 8,695,607 | B2 | 4/2014 | Hohenhorst | |
| 8,851,078 | B2 | 10/2014 | Newman et al. | |
| 2005/0247309 | A1 | 11/2005 | Reddick | |
| 2007/0079832 | A1 | 4/2007 | Baldauf et al. | |
| 2007/0181135 | A1* | 8/2007 | Baker | A61F 5/56 128/848 |
| 2008/0156332 | A1* | 7/2008 | Ray | A61F 5/055 128/845 |
| 2008/0163875 | A1* | 7/2008 | Aarestad | A61F 5/56 128/846 |
| 2008/0223377 | A1* | 9/2008 | Kussick | A61F 5/56 128/869 |
| 2009/0095309 | A1 | 4/2009 | Derrick et al. | |
| 2010/0294284 | A1* | 11/2010 | Hohenhorst | A61F 5/012 128/848 |
| 2011/0220113 | A1* | 9/2011 | Newman | A61M 16/0683 128/206.24 |
| 2012/0234330 | A1 | 9/2012 | Saiz | |
| 2015/0164726 | A1 | 6/2015 | Ward et al. | |
| 2018/0008452 | A1* | 1/2018 | Wade | A61F 5/56 |

FOREIGN PATENT DOCUMENTS

| | | | | |
|---|---|---|---|---|
| DE | 102005025996 | B3 * | 4/2006 | A61M 16/0409 |
| EP | 1981431 | B1 | 7/2014 | |
| GB | 2267034 | A | 11/1993 | |
| WO | 2009129081 | A1 | 10/2009 | |
| WO | 2012024728 | A1 | 3/2012 | |
| WO | 2021049941 | A1 | 3/2021 | |

OTHER PUBLICATIONS

International Search Report and Written Opinion for corresponding International application No. PCT/NL2020/050567; dated Dec. 3, 2020 (16 pages).

Communication under Rule 71(3) issued in corresponding European patent application No. 20 775 432.6-1122; dated Nov. 12, 2024 (6 pages).

International Search Report and Written Opinion for corresponding International application No. PCT/EP2024/050412; Mar. 19, 2024 (19 pages).

International Preliminary Report on Patentability for corresponding International Application No. PCT/EP2024/050412; dated Apr. 4, 2025 (12 pages).

* cited by examiner 37
39
$H_p$
30
32
41B
41A
41
29
F
23
15
$W_p$
$W_m$
A
A
P
45
$D_F$ 30
29
32
41A
41B
41
F
23
15
$H_p$
$W_p$
$W_m$
$W_b$
A
A
P
45
37
39

37
39
47
49
SP
IP
$H_D$
$H_V$
41
43
49
45
49

50
39
45
47
52
49
43
54

39
45
47
52
49
43

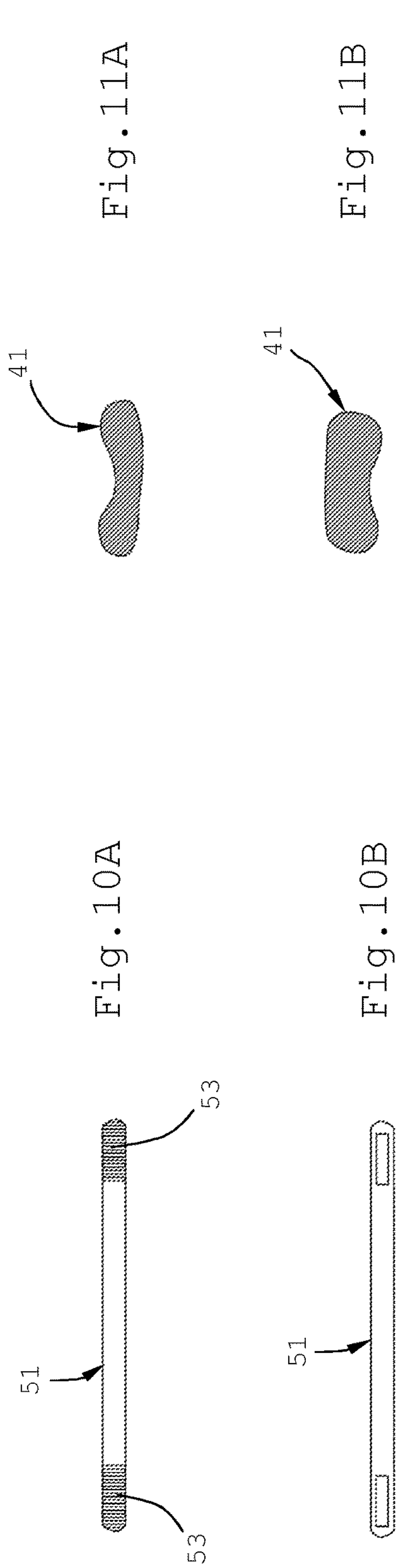
Fig.11A
41
Fig.11B
41
Fig.10A
53
51
53
Fig.10B
51
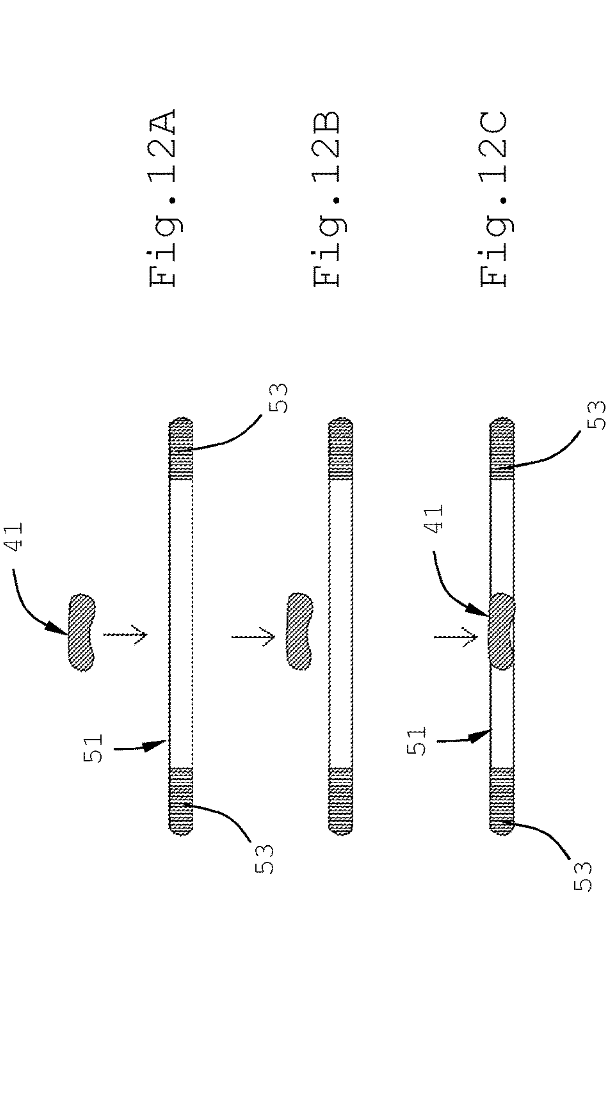
Fig.12A
Fig.12B
Fig.12C
41
53
51
53
41
53
51
53

VENTILATION ASSEMBLY AND HARNESS

TECHNICAL FIELD

The present disclosure relates to a head wearable harness, and in particular to a head wearable harness for use in medical procedures where a laryngeal mask is used for ventilation of a person.

BACKGROUND

Medical treatment of persons may involve attachment of one or more objects to the person's head, which object(s) may require prolonged fixation. Commonly, this is done by use of plasters and/or bandages. However, bandages may loosen affecting fixation and plasters may be incompatible and/or may damage the person's skin. Further, provision of and/or checks of accurate positioning of the object(s) may be hindered by such solutions. A balance should be found between reliable attachment and possibly fixation of the object(s) to the person, user comfort for the treated person, application comfort for medical personnel and minimal negative interaction with any treatment.

As a specific case, persons incapable of normal breathing, e.g. when injured and/or sedated, may be subject to mechanical ventilation. Intubation is a well-known forced ventilation technique. The use of a laryngeal mask for forced ventilation is also well established and it is generally preferred over intubation as less invasive. Various (aspects of) laryngeal masks are disclosed in e.g. WO 2012/024728. Although laryngeal masks have been developed to effectively seal against the larynx, such sealing may not be perfect and leakages of air do still persist, for example, due to differences in a patient's anatomy relative to available mask shapes and sizes. Leakages may be due or worsened by sedation and muscle relaxation. Such leakages may affect control of amounts of ventilated air and/or control of a composition of ventilation air mixtures, which may e.g. contain one or more of moisture, sedatives, diagnostic substances and/or medicaments relative to ambient air. Such leakages should therefore be prevented.

In practice, in case leakages of a laryngeal masks are found and persist, possibly after repeated reapplication, practitioners tend to use a laryngeal mask of a bigger size, i.e. a size up. However, if leakages even then still persist and/or if such larger laryngeal mask does not fit, intubation is used after all.

It is therefore desired to prevent such leakages and/or to increase the possibility of effective usage of laryngeal masks.

GB 2 267 034 discloses a laryngeal airway clamp, wherein a laryngeal mask airway device is clamped in position by a clamping member engaging the neck of a patient in opposition to the laryngeal mask of the device. The clamp engaging the neck presses against the airway and part of the clamp extends into the mouth and larynx of the patient which may interfere with access to the airway and/or with treatment of the patient.

It is further noted that several devices are known for establishing and maintaining the lower jaw or mandible of a subject in a desired position relative to the upper jaw but unrelated to and/or incompatible with laryngeal masks (see also below). E.g. US 2018/0008452 relates to a device to urge the mouth closed during sleep to reduce snoring and/or treat sleep disorders such as sleep apnea. In one aspect, the device includes a jaw-blocking object that is secured beneath the chin of a user and also contacting the clavicular region of the upper chest area. In another aspect, a device of the invention includes a jaw-blocking object in combination with a Continuous Positive Airway Pressure (CPAP) mask and headgear for use with a CPAP system. The CPAP mask is worn on the face of the user, thus being in contrast to a laryngeal mask which is inserted into the larynx of the user.

SUMMARY

In view of the above, a ventilation assembly and a head wearable harness as specified herein are provided.

Thus, in an aspect, a ventilation assembly is provided, the ventilation assembly being for use in ventilating a mammalian subject using a laryngeal mask, in particular forced ventilation of the subject. The subject may be a primate, more in particular a human person. The assembly comprises a head-wearable harness and a pusher. The harness is arrangeable on the subject's head for supporting the pusher against the floor of the mouth of the subject, the pusher being arranged to provide local elevated pressure in cranial direction between lateral sides of the mandible to soft tissue of the floor of the mouth and to displace soft tissue of the floor of the mouth in cranial direction of the portion relative to the mandible of the subject for, when the laryngeal mask is installed in the airway of the subject, urging internal soft tissue of the subject against the laryngeal mask in the airway of the subject as a seal to the mask. The pressure is in particular locally elevated relative to a pressure at or near the mandible of the subject. The harness may in particular be a harness as specified herein.

Thus, the assembly is arranged to urge the airway of the subject closed against the laryngeal mask in the airway. Therewith the body tissue is used to seal the airway and prevent leaks along the laryngeal mask. This may allow use of relatively small laryngeal masks and/or use of laryngeal masks otherwise poorly fitting the patient's anatomy.

A head wearable harness, i.e. a harness that is, in use, attached to and/or supported on subject's head on its own, without requiring external assistance, just like hats, glasses, masks, scarfs, etc., allows reliable positioning of the pusher against the floor of the mouth, independent of the position and/or the movement of the patient's head.

A head wearable harness also obviates use of external devices such as e.g. those taught by U.S. Pat. No. 7,047,977 for a medical device for overcoming airway obstruction by the tongue of a sedated or unconscious patient lying in the supine position.

The head-wearable harness may have a superior portion and an inferior portion, wherein the superior portion is arrangeable on a subject's head, e.g. being arranged to at least partially encircle and/or cover the top and/or crown of a subject's head, and the inferior portion is arranged to support the pusher, wherein the pusher comprises a protrusion towards the superior portion for displacing the soft tissue and/or is configured to form a protrusion towards the superior portion for displacing the soft tissue of the floor of the mouth. The protrusion is configured to be, in use, protruding in cross section in a frontal plane.

Also or alternatively, the pusher may be wedge shaped in cross section in a sagittal plane. A thickness and/or height of the protrusion may vary in sagittal direction corresponding to the wedge-shape and/or defining the latter.

The inferior portion may be arrangeable under the lower jaw of the subject. The harness may be fixed to the subject's head by the superior portion and/or by the combination of the superior and inferior portions. The protrusion may be configured to fit at least partly within the body and/or angle of an average human mandible, possibly configured to fit at least partly within the body and/or angle of an average human mandible of persons or groups with specific group characteristics such as age, sex, medical condition etc. Such assembly provides a displacement force at least predominantly on the soft tissue of the floor of the mouth for displacement thereof within and/or through the mandible in the desired direction. The embodiment may be configured to displace the soft tissue such that, in use, the outer surface, i.e. the skin, of the floor of the mouth is pushed further than, or at least to about level with, the underside of the soft tissue covering the body of the lower jaw. The further the floor of the mouth is pushed into and between (the angle and/or body portions of) the mandible, the more sealing pressure may be applied onto the laryngeal mask.

At least one of a size, a shape, a position and an orientation of at least part of the pusher may be adjustable, in particular reversibly adjustable, relative to the harness. Thus, the ventilation assembly may be adapted to a subject's anatomy and/or to accommodate further (medical) apparatus associated with a medical procedure and/or the subject, e.g. supports, braces, surgical tools, etc. E.g., the pusher may comprise an inflatable portion. Also or alternatively, at least part of the pusher may be formed resilient such as by comprising a portion of an elastically compressible material. Thus, when engaging the floor of the mouth of a subject to be treated, the pusher may at least partly (elastically) deform and adapt to the subject's anatomy, in particular the shape of (the body and/or angle of) the subject's mandible. It is noted that adaptation of the pusher and/or the harness to the anatomy of the subject to be treated may improve reliable positioning of the assembly and/or may prevent complications such as tissue damage from (local) excessive pressure and/or obstructed blood vessels.

The ventilation assembly may further comprise mated connectors for attaching and/or detaching, in particular reversibly, at least part of the pusher to the harness. This facilitates individual cleaning, replacement and/or exchange at least part of the harness and/or, respectively, at least part of the pusher. In an embodiment, at least part of the pusher may be modular for adjustment of the sized and/or shape of the pusher.

The pusher may be V-shaped or kidney-shaped or chevron-shaped for, in situ under a subject's lower jaw, accommodating a portion of the subject's throat. The V-, or kidney- or chevron-shape being, in use, in a transverse plane. Such shape, e.g. the opening provided between opposing "legs" of a V- or chevron-shape, which may generally conform to an average subject's mandible, may prevent or relieve pressure on the subject's throat. The pusher may be configured to conform to, or fit at least partly within, an average human mandible, possibly subject to specific group characteristics as indicated above.

The harness may have a superior portion and an inferior portion, wherein the superior portion is arrangeable on a subject's head, e.g. being arranged to at least partially encircle and/or cover the top and/or crown of a subject's head, and the inferior portion is arranged for supporting the pusher, wherein at least the inferior portion comprises one or more flexible members operably connected or connectable to the pusher. Also or alternatively, the superior portion may comprise one or more flexible members, in particular bands etc. as indicated above, operably connected or connectable to the inferior portion. The harness may be attached, in particular fixed, to the subject's head by the superior portion and/or by the combination of the superior and inferior portions. The flexible members may be bands, belts and/or any other suitable members, e.g. strings, chains, etc. Flexible members facilitate adaptation of the harness to a subject's anatomy, e.g. improving user comfort and/or prevention of localised pressure. Flexible members may aid the ease of installation and/or may improve the consistency of the tension with which the harness is arranged on the subject's head and in particular of a force with which the pusher may be pushed against the lower jaw, such as, more in particular, a force in cranial direction.

In any harness discussed herein, a superior portion of the flexible member may be arrangeable on the subject's head cranial of the ears, and an inferior portion of the flexible member may be arrangeable under the subject's lower jaw, and in particular being arrangeable frontal of the subject's ears. This may assist prevention of tissue damage and/or avoiding covering the subject's temples by the flexible member, facilitating access to the face and/or attachment of e.g. electrodes to the temples.

In an aspect, the harness may comprise a flexible member configured to partially or fully encircle a subject's head in a plane generally parallel to an anatomic transversal plane. Thus the one or more flexible members of the superior portion may run, in use, at least partially, over the subject's forehead, along the sides of the head above or over the top of the ears, and across the back of the head. Also or alternatively, the harness may comprise a flexible member configured to partially or fully encircle a subject's head in a plane generally parallel to an anatomic coronal plane. Such flexible member may run, in use, at least partially, over the top of the head, over the temple and underneath the lower jaw of a subject.

The flexible member or members may form part of the superior portion. Such flexible member(s) may serve for attachment and in particular for fixation of the harness to the subject's head, by which the pusher may be attached, in particular fixed, in a desired operative position.

In particular in an assembly comprising a flexible member, the harness may comprise at least one fastener for size adjustment of the harness, e.g. a length adjustment of the flexible member. The fastener itself may be adjustable. Thus, the harness may be more easily arranged, fit and/or fixed on a subject's head. Suitable fastener may be, for example, a buckle, a hook-and-loop-type fastener, e.g. of the type commonly referred to as Velcro®, etc. An openable fastener may facilitate donning of the harness to a subject without interference of or complications of apparel attached to the subject, such as an intubation tube device and/or an endoscope etc.

Further, the assembly may be provided together with a laryngeal mask and/or a selection of different sized and/or shaped pushers and/or pusher inserts, all or any of them in a sterile package. This facilitates planning and/or execution of treatment.

The provided assembly is easily applicable by a subject positioned at the head end of a subject lying in supine position and it provides substantially free and unobstructed access to parts of the subject's body uninvolved in the ventilation procedure. E.g. application of the assembly may prevent discontinuation of the ventilation procedure since a ventilation tube need not be removed for application of the assembly.

The assembly may be for single use or, at least in part, for repeated use, in which case the respective part may be cleanable, desinfectable and/or sterilisable in a generally known manner.

In an aspect a head wearable harness is provided. The harness may in particular be a head wearable harness for the ventilation assembly disclosed herein. The harness is wearable on the subject's head for supporting, and in particular fixing, one or more objects on the subject's head, e.g. the pusher of the assembly.

The harness has a superior portion and an inferior portion, wherein the superior portion is arrangeable on the subject's head superior of the subject's ears and the inferior portion comprises one or more flexible members, in particular bands, arrangeable underneath the subject's chin or lower jaw. The harness comprises a flexible member configured to partially or fully encircle the subject's head generally parallel to an anatomic coronal plane and the harness is configured to leave, in use, the head uncovered by the harness frontal of the flexible member.

A head wearable harness, i.e. a harness that is, in use, attached to and/or supported on subject's head on its own, without requiring external assistance, just like hats, glasses, masks, scarfs, etc., allows reliable positioning of the object to the head, independent of the position and/or the movement of the patient's head and it may be relatively easy to put on the subject and to fit to the subject's anatomy, supporting a pusher and/or further objects while leaving the frontal portion of the head, e.g. the face and forehead, free for access by care givers and/or for apparel like monitoring electrodes.

In any of the harnesses described herein at least part of the inferior portion may be substantially elastic and at least part of the superior portion may be substantially non-elastic. In particular, the inferior portion may comprise one or more flexible members, in particular bands, being arrangeable under the subject's lower jaw and having an elastic portion, and the superior portion may comprise one or more flexible members, in particular bands, being arrangeable superior of the subject's ears and being substantially non-elastic. This facilitates adjustment of tension on the generally relatively soft inferior part of the head, e.g. cheeks, chin, etc., while positioning the superior portion on the generally harder and more robust of the head. The (non-)elasticity should be considered relative to each other, e.g. the inferior portion comprising one or more portions of soft (artificial) rubber, latex, neoprene, tricot, stretch cloth, etc. alone or in combination, whereas the superior portion comprising one or more portions of a flexible substantially inelastic material like one or more of hard (artificial) rubber, canvas, woven cloth, chain, etc.; and/or a difference between fewer and more layers of the same elastic material providing significantly different degrees of elasticity for the portions. As also discussed elsewhere herein, the harness and its material(s) must be compatible with being in contact with, and worn on, mammalian, in particular human, skin for extended periods and preferably being flexible for deformation and accommodating the subjects anatomic features.

In any harness discussed herein, one of the superior portion and the inferior portion of the harness may comprise an opening and/or a hook, and the other one of the superior portion and the inferior portion of the harness may comprise a flexible member provided with a looping-back portion, wherein the looping-back portion may form or may be formable as a loop through the opening and/or the hook, the looping-back portion being attachable or attached to itself to close the loop for at least locally fastening the superior and inferior portions together. This facilitates arranging the harness on the head and any object attached to it, e.g. the aforementioned pusher.

In an aspect a method of ventilating a subject is provided comprising operably installing a laryngeal mask in the airway of the subject, and urging internal soft tissue of the subject against the laryngeal mask in the airway of the subject for at least partly sealing the airway and preventing leaks along the laryngeal mask by urging soft tissue of the floor of the mouth of the subject in a cranial direction of the subject relative to the mandible of the subject.

The method may preferably comprise providing the subject with a ventilation assembly as disclosed herein and arranging, by appropriate positioning and/or orienting the pusher of the ventilation assembly to displace the soft tissue of the floor of the mouth of the subject in cranial direction of the subject.

The method may comprise deforming the pusher in accordance with at least one anatomic characteristic of the subject, e.g. a size and/or shape of the subject's mandible.

It is noted that several devices are known for establishing and maintaining the lower jaw or mandible of a subject in a desired position relative to the upper jaw, which all are configured and destined to overcoming obstructions of the airway, rather than urging the airway closed for sealing against a laryngeal mask as explained above. Such devices are therefore not related to use with forced ventilation.

E.g., US 2005/0247309 and US 2009/0095309 disclose rigid support devices for thrusting the jaw of a patient forwardly from the patient's chest to permit the patient to breathe freely during sedation or sleeping. Their operation depends on the patient's posture and (im-)mobility.

US 2010/0294284 discloses apparatus, systems, and methods which constrain and/or support tissue structures along an airway by wearing a support collar. A collar hinders access to the throat and/or restricts the wearer's mobility.

US 2007/0079832, and US 2015/0164726 are frames mounted near the patient's head for assisting respiration of a patient. The devices are configured for thrusting the jaw of a patient forwardly to permit the patient to breath freely during sedation or sleeping.

U.S. Pat. No. 7,124,758 discloses a device for treating snoring and obstructive sleep apnea. The device of U.S. Pat. No. 7,124,758 comprises a headband and two belts. The headband is placed on the head of a user and the belts are attached to the front of the headband, the belts are crossed over the top of the users head and then are made to go from the back of the users neck to cross under the users chin and then to attach to the front part of the headband. The device, in use, maintains sufficient tension to keep the jaws of the user locked together and the front teeth of the lower jaw in contact with the front teeth of the upper jaw and overcomes obstructions of the airway so that obstructive sleep apnea is relieved and associated morbidity is reduced.

BRIEF DESCRIPTION OF THE DRAWINGS

The above-described aspects will hereafter be more explained with further details and benefits with reference to the drawings showing a number of embodiments by way of example.

FIGS. 10A-10B are a top view and a bottom view, respectively, of a band for fixing a pusher to a harness according to FIGS. 6-8;

FIGS. 11A-11B are a side view and a top view of a pusher as disclosed herein;

FIGS. 12A-12C show assembly of the band and pusher of FIGS. 10A-10B and 11A-11B for forming the ventilation assembly of FIGS. 7-8.

DETAILED DESCRIPTION OF EMBODIMENTS

Figure 1A:
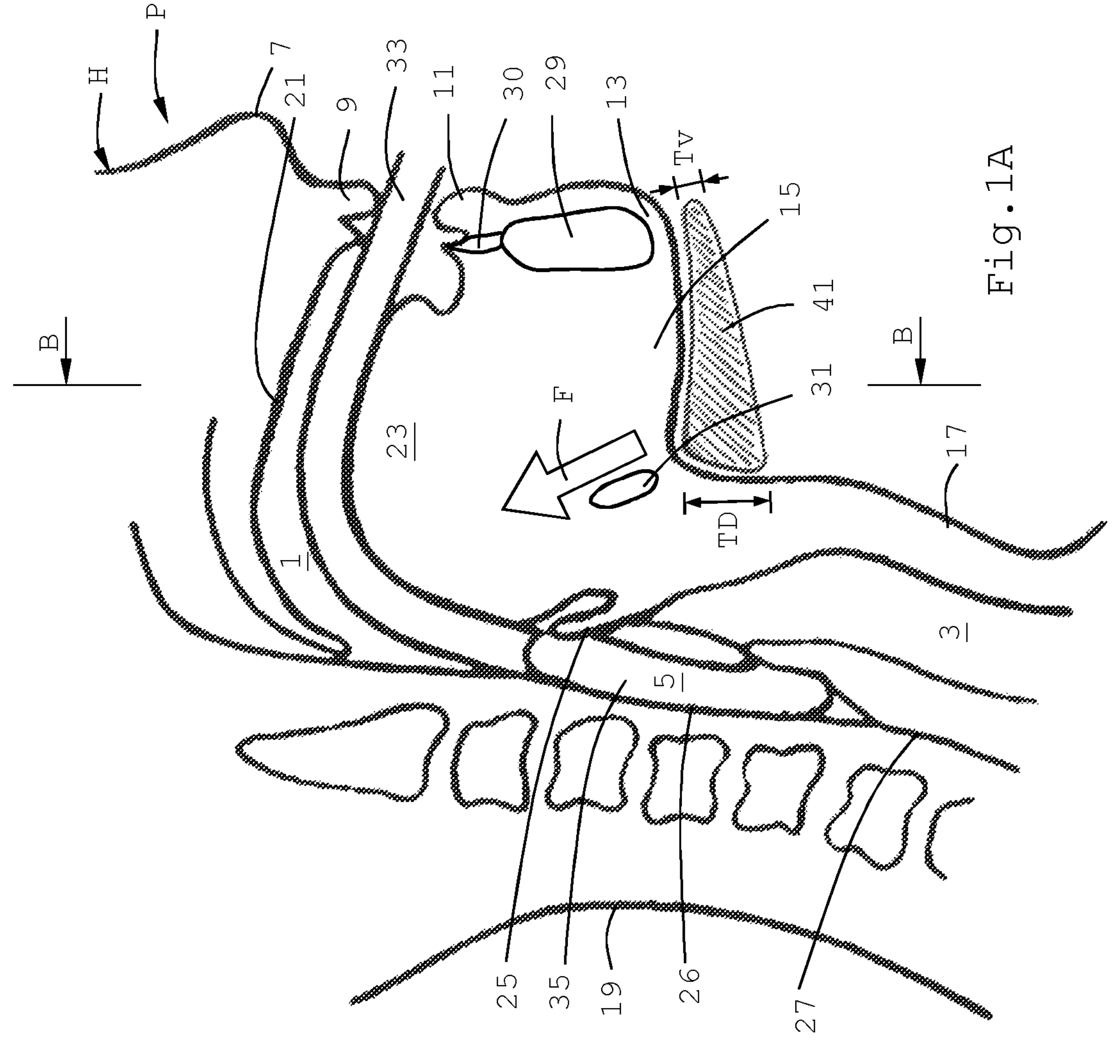
FIG. 1A is a partial schematic cross section of a human neck area with a laryngeal mask inserted in operative position, also including part of a ventilation assembly as disclosed herein.

It is noted that the drawings are schematic, not necessarily to scale and that details that are not required for understanding the present invention may have been omitted. The terms "upward", "downward", "below", "above", and the like relate to the embodiments as oriented in the drawings, unless otherwise specified. Further, elements that are at least substantially identical or that perform an at least substantially identical function are denoted by the same numeral, where helpful individualised with alphabetic suffixes.

Figures 1B, 1C:
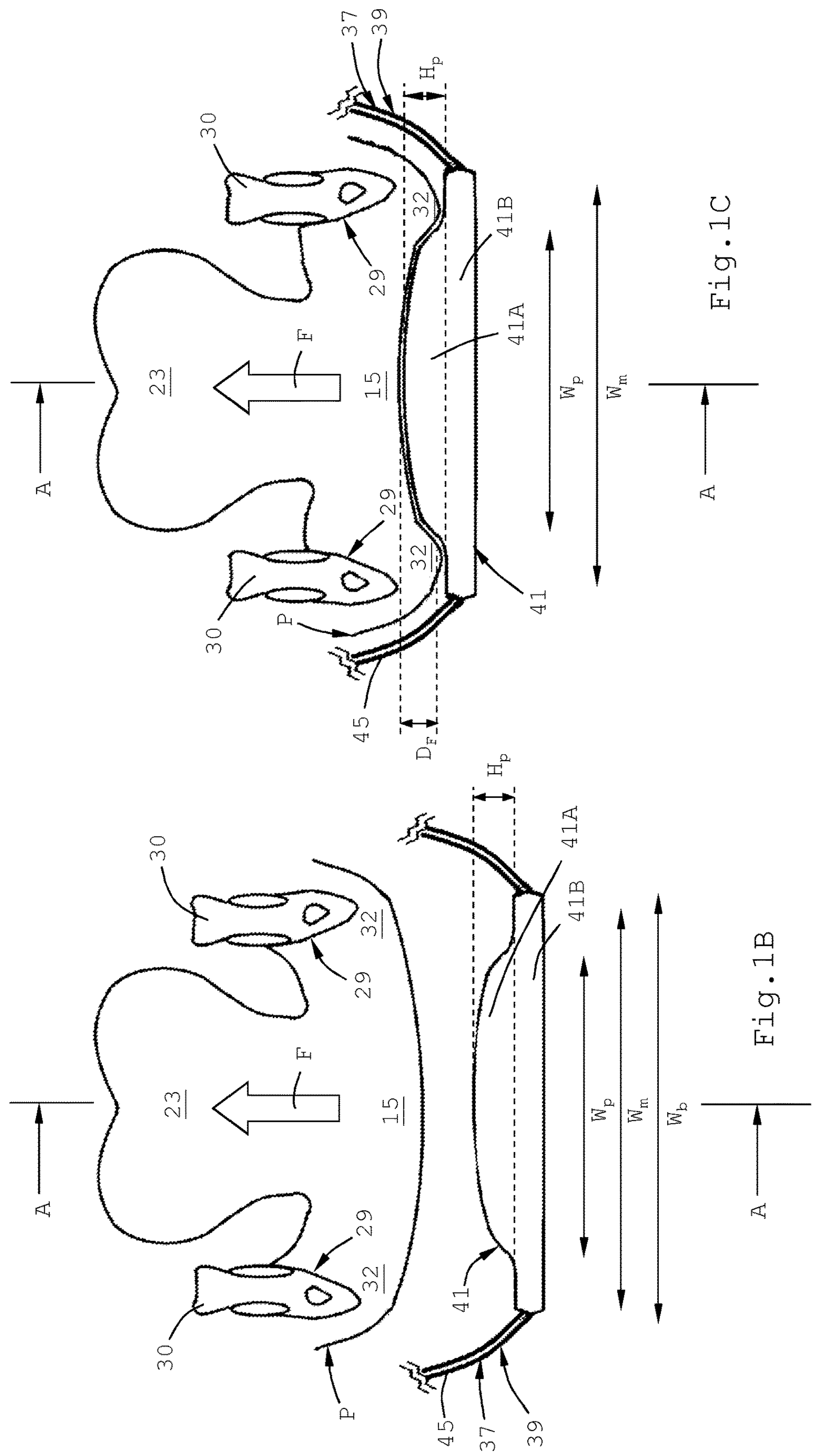
FIG. 1B is a partial schematic cross section, along plane BB indicated in FIG. 1A, of a human neck area also including part of a ventilation assembly as disclosed herein.
FIG. 1C is a partial schematic cross section, along plane BB indicated in FIG. 1A, of a human neck area also including part of a ventilation assembly as disclosed herein in operative position.

FIGS. 1A-1C are partial schematic cross sections of a lower head and neck area of a person P, according to sagittal plane AA (FIG. 1A, plane indicated in FIGS. 1B and 1*n* FIG. 1C) and frontal plane BB (FIG. 1B, FIG. 1C, plane indicated in FIG. 1A). These figures (predominantly FIG. 1A) show the pharynx 1, larynx and trachea 3 of a person P with a laryngeal mask 5 inserted in the airway (nose and/or mouth-pharynx-larynx-lungs) of the person P in operative position. Discernible are the person's nose 7, upper lip 9, lower lip 11, chin 13, floor of the mouth 15, and throat 17, as well as the back of the neck 19. Further are discernible the person's palate 21, tongue 23, pharynx 1, epiglottis 25, laryngopharynx 26 and esophagus 27, as well as the mandible 29 with teeth 30 and the hyoid bone 31. Jaw tissue 32 (in particular gingivae) separates the soft tissue of the floor of the mouth 15 from the soft tissue of the person's cheeks and mouth. The soft tissue of the floor of the mouth 15 is predominantly formed by the left and right submandibular triangles (trigonum submandibulare) and the submental triangle (trigonum submentale). The laryngeal mask 5, connected to a ventilation tube 33, is inserted in the laryngopharynx 26 in usual manner and covers the opening of the trachea 3. The laryngeal mask 5 comprises an inflatable cuff 35 for generally sealing off (the opening of) the trachea 3. Thus positioned and if properly fit, the patient person P can be forcedly ventilated through the tube 33 connected to the mask 5.

Figure 7:
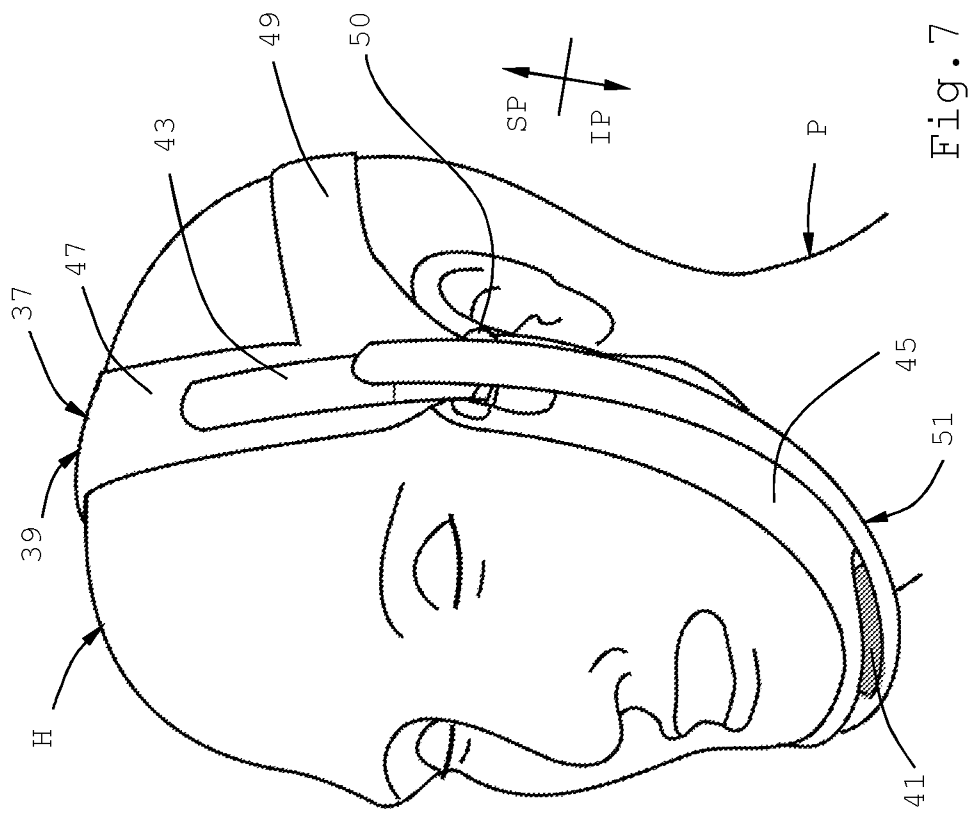
FIGS. 7-8 are side view and a front view, respectively, of a person wearing a ventilation assembly including the harness of FIG. 6.
Figure 8:
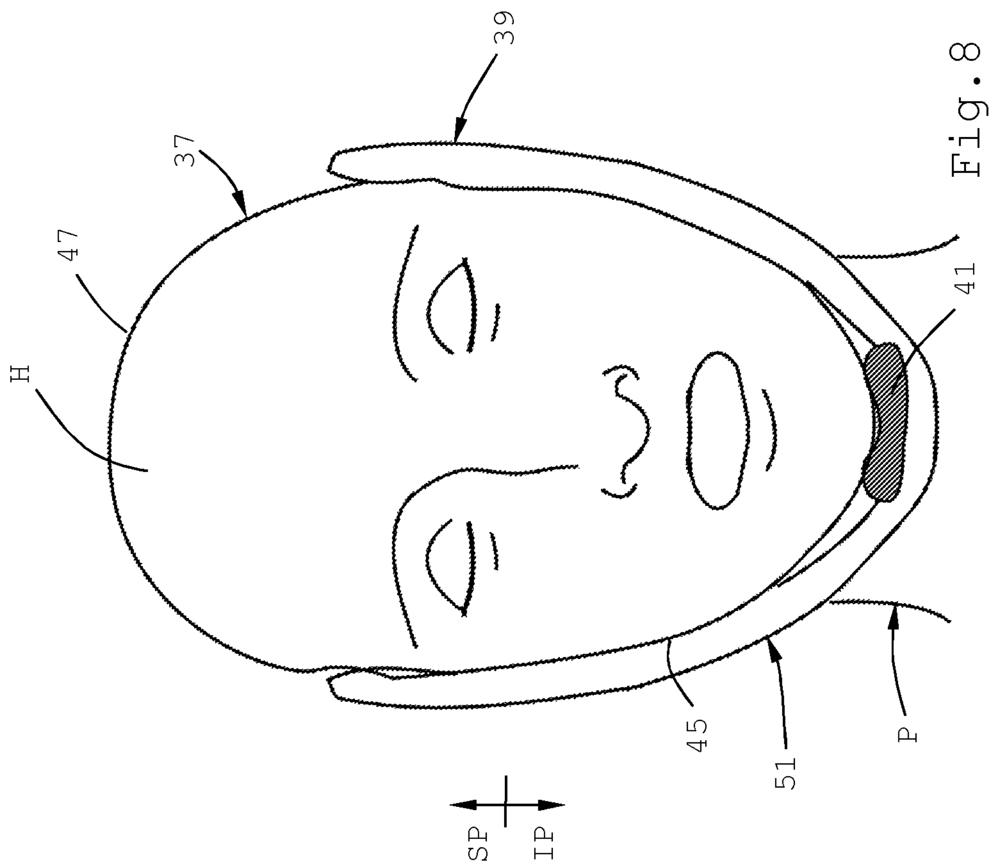

In order to reduce or prevent leaks in case of an otherwise improper sealing of the mask 5 in the laryngopharynx 26, the ventilation assembly 37 is provided, of which (use of) an embodiment is shown in FIGS. 2-5. A further embodiment is shown in FIGS. 7-8. The ventilation assembly 37 comprises a head-wearable harness 39 and a pusher 41. An embodiment of the latter is visible in FIGS. 1A-1D. Note that in FIGS. 1A-1C for clarity the ventilation assembly 37 is shown spaced from the person's head; in operation the assembly will be in close contact with the skin.

The harness 39 is arrangeable on the head H of the person P for supporting the pusher 41 against the floor of the mouth 15 of the person P; see FIGS. 1A-1C and FIGS. 2-3. The pusher 41 is arranged to displace soft tissue of the floor of the mouth 15 in cranial direction relative to the mandible 29 of the person P, see arrow F in FIGS. 1A-1C. This force direction is in or parallel to the sagittal plane, inclined to the coronal direction generally from the floor of the mouth 15 to the person's ear, crossing the entrance (introitus) of the ear canal or across a rear (dorsal) half of the temple in front of (ventral of) the ear canal. Thus, when the laryngeal mask 5 is installed in the airway of the person P as shown in FIG. 1A, the pusher 41 is arranged for urging internal soft tissue of the floor of the mouth 15 of the person P, e.g. parts of the tongue 23 and/or epiglottis 25, against the laryngeal mask 5 in the airway of the person P, without choking or otherwise impairing breathing of the person P. As will be clear from FIGS. 1A-8, the ventilation assembly requires little space below the chin and does not interfere with access to the chest and/or the neck areas. E.g. the (pusher of the) assembly may be arranged above (cranial of) the thyroid (cartillago thyroidea), as shown, and/or above (cranial of) the hyoid. Such assembly also keeps the neck area accessible for (emergency) tracheotomy.

Figure 2:
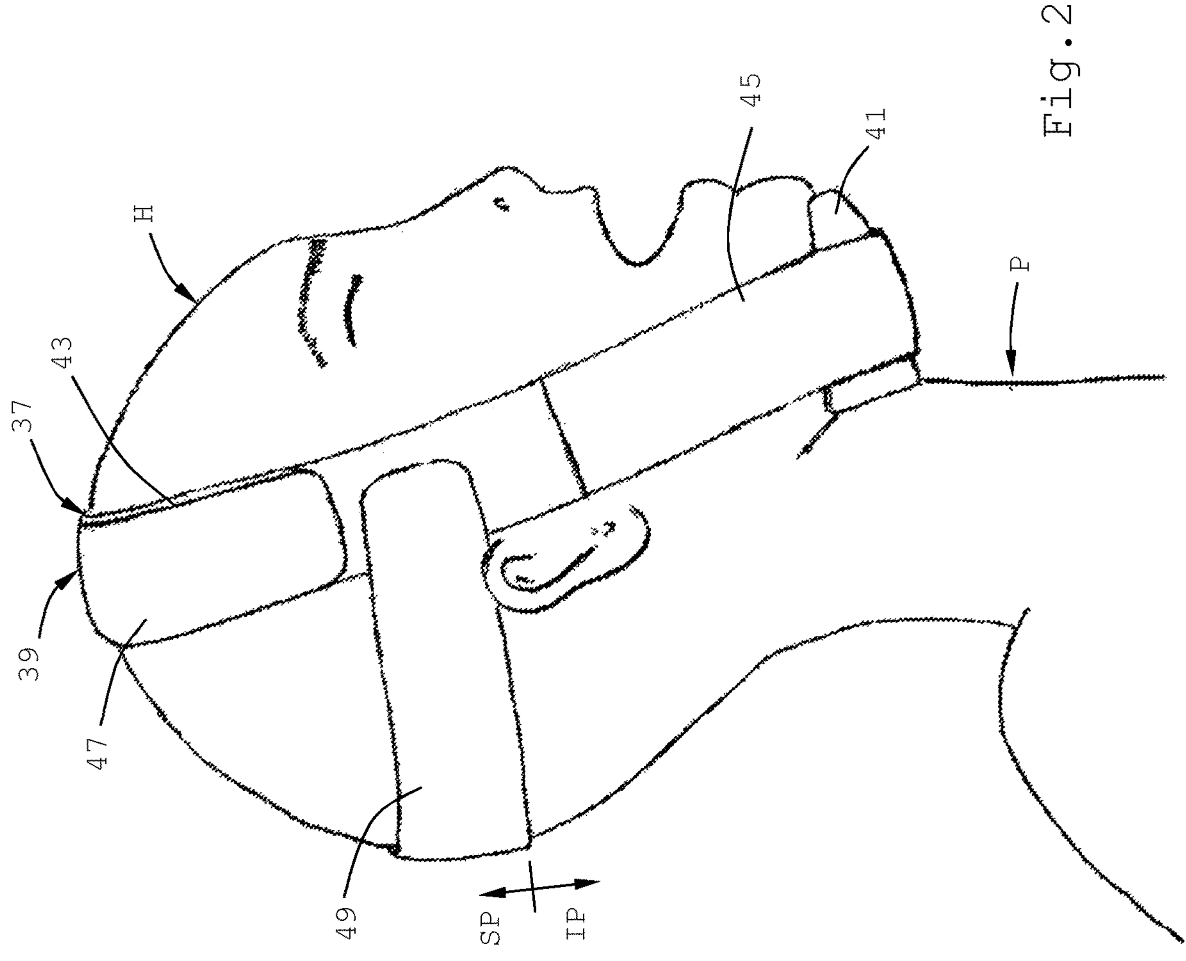
FIG. 2 is a side view of a person wearing a ventilation assembly as disclosed herein.
Figure 3:
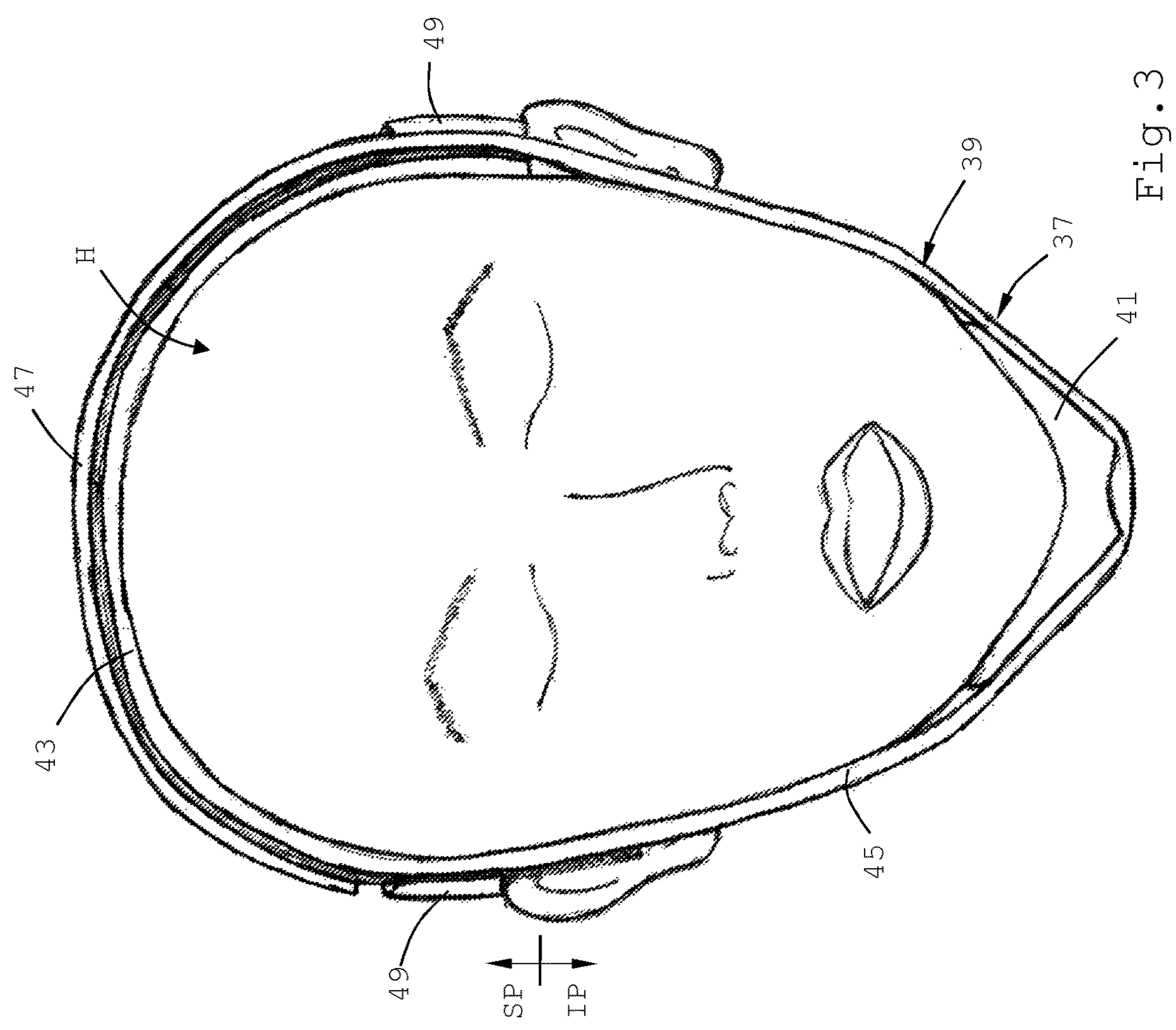
FIG. 3 is a front view of a person wearing a ventilation assembly as disclosed herein.
Figure 4:
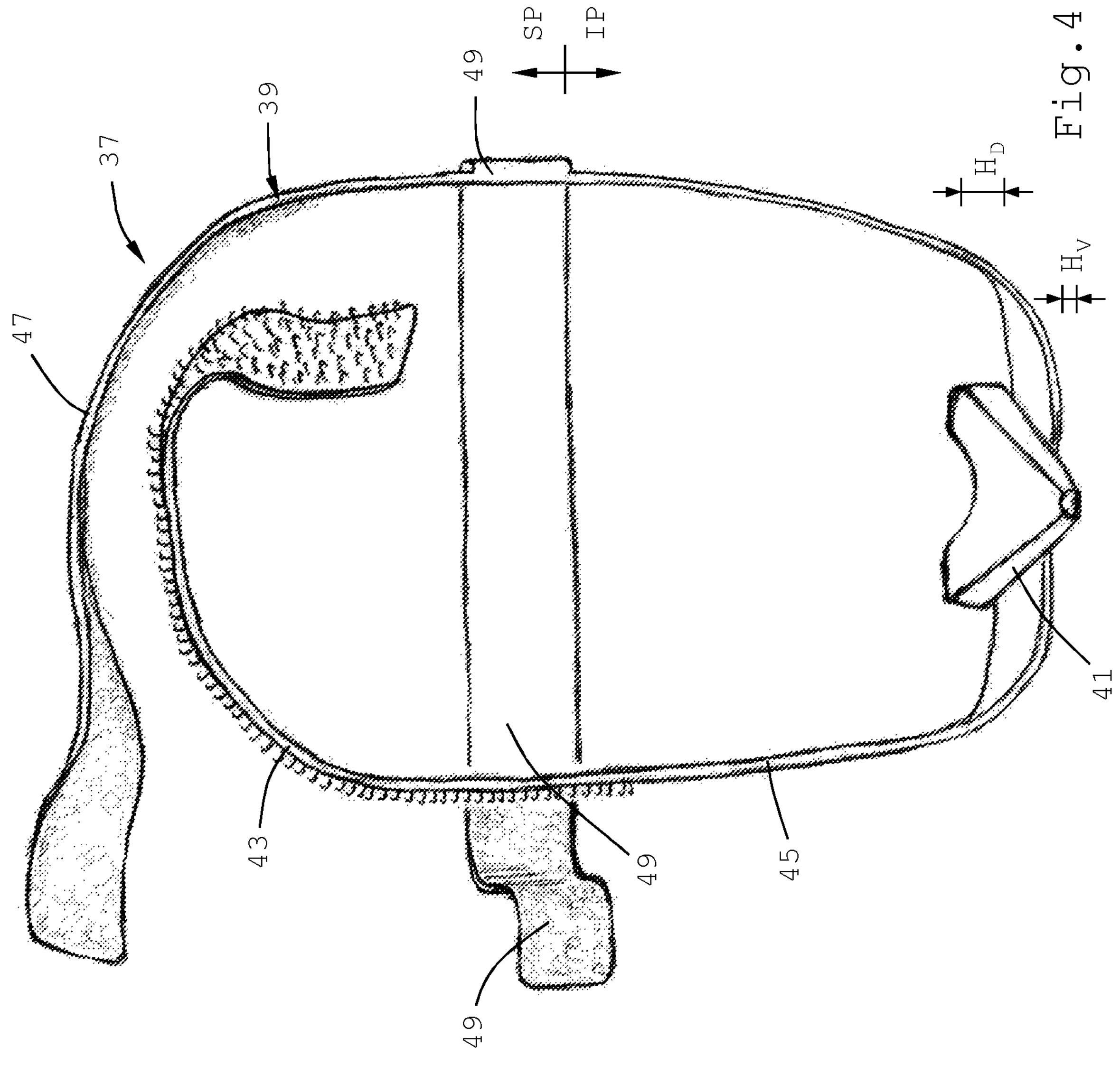
FIG. 4 is a front view of a ventilation assembly as disclosed herein.
Figure 5:
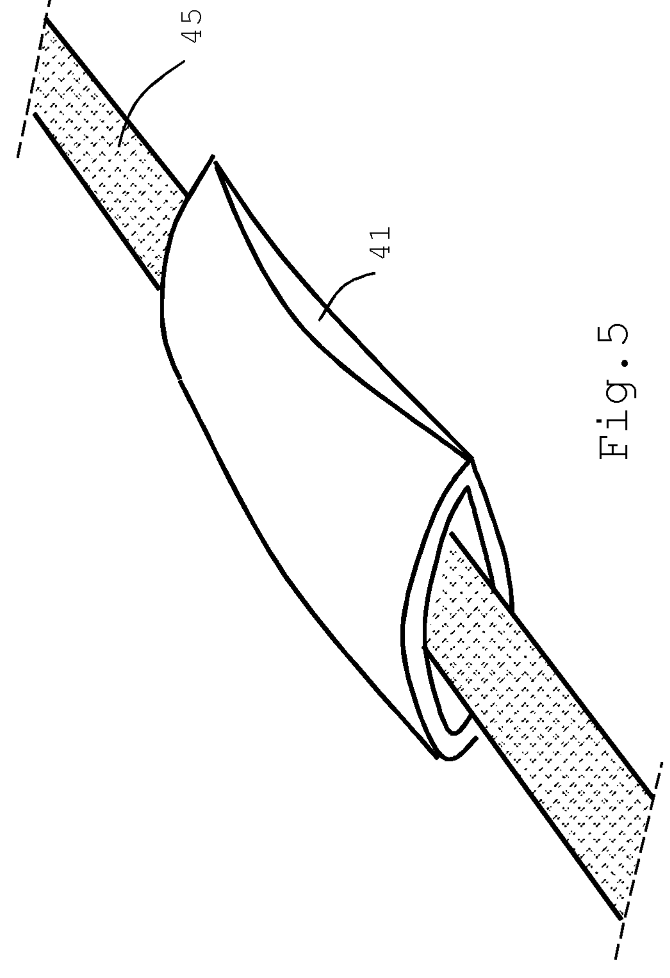
FIG. 5 shows an embodiment of part of a harness and a pusher.

The harness 39 has a superior portion SP and an inferior portion IP, generally and non-limitatively indicated in FIGS. 2-4. The superior portion SP is arrangeable on the person's head H for attaching, in particular fixing, the assembly to the head H. The inferior portion IP is attached to the superior portion SP and supports the pusher 41, such that, in use, the pusher 41 may be reliably positioned under a person's lower jaw for engaging the person's floor of the mouth 15 and urging the soft tissue of the floor of the mouth 15 in the proper direction F as explained above. The shown pusher 41 provides a protrusion on the inferior portion IP towards the superior portion SP. The direction of the force F may be such that the teeth 30 of the person (in a normal healthy individual with average anatomic shape) are aligned in a normal biting position with the lower teeth behind (i.e. dorsal of), but close to, the upper teeth; no "overbite". The effect and the resulting position may be referred to as "jaw thrust". A so-called "chin-lift" position wherein the lower teeth may pass and become positioned in front of (i.e. ventral to) the upper teeth is considered best to be prevented.

As shown, the superior portion SP and the inferior portion IP comprise flexible members in the form of band sections 43, 45, 47, 49, facilitating adaptation of the harness 39 to the anatomy of the person P wearing (the harness 39 of) the assembly 37. As shown, at least some of the flexible band sections 43, 45, 47, 49 may be formed as continuations of each other which may facilitate manufacture. Also or alternatively at least some flexible members, e.g. plural band sections 43, 45, 47, 49, could be formed as separate members attached to each other with fasteners which may be repeatedly openable and closable for adjustment and/or reuse.

In the shown harness 39 the combined band sections 43, 45, 47 form one band encircling, in use, the person's head H generally in an anatomic coronal plane. A transverse band section 49 provides a band encircling, in use, the person's head H generally in an anatomic transverse plane. Besides fixing the assembly 37 on the person's head H, the (coronal) band sections 43, 45, 47 assist positioning the pusher 41 and providing a main component of the force F in superior direction, the transverse band section 49 prevents the (coronal) band sections 43, 45, 47 from displacement in the anterior direction and/or it assists adjusting the force F in a dorsal direction. A transverse band may encircle the head fully, but it preferably encircles the head H only partially so and above one or both ears of the person P so that at least part of the person's face and/or forehead and/or ears are unobstructed, e.g. for devices and systems like thermometers and/or sensors for monitoring of brain activity. However, other harness shapes may be provided, including harnesses in which the superior portion SP is generally cap- or hat-shaped, and or wherein the superior and/or inferior portion IP comprises several bands, e.g. running in a web-shape or in a general V- or Y-shape shape across the person's cheeks with the tip or apex of the shape towards the pusher.

The harness 39 may be closed and may comprise one or more elastic portions. The shown harness 39 comprises optional fasteners for size adjustment of the harness 39, e.g. a length adjustment of flexible members, e.g. one or more band sections 43, 45, 47, 49. FIGS. 2-5 indicate hook-and-loop-type entanglement fasteners V e.g. such as commonly called "Velcro", in such case the hook-side should preferably be oriented outwardly, away from the person's skin (FIG. 4). However, fasteners may take any suitable form or combination, e.g. comprising one or more of buckles, clasps, buttons, slides, zippers, D-ring fasteners, etc.

Figure 1D:
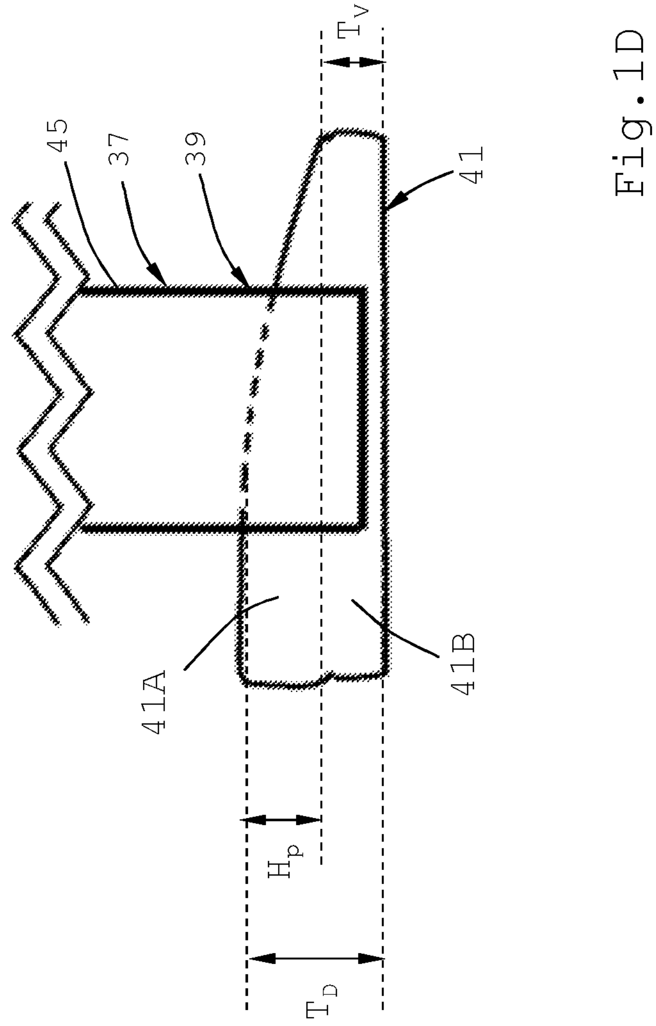
FIG. 1D is a side view of part of a ventilation assembly as disclosed herein.

As most clearly visible in FIG. 4, the pusher 41 may be generally V-shaped in transverse direction, having a vertex at a front (in use: ventral) side and a space between opposing legs at a rear (in use: dorsal) side. Thus, in situ under a person's lower jaw part of the person's throat can be accommodated in the opening of the V-shape of the pusher 41. Further, as best seen in FIGS. 1A, 1D and 2, the pusher 41 may have a relatively thick rear (in use: dorsal) side of thickness $T_D$ and a relatively thin front (in use: ventral) side of thickness $T_V$ so that the pusher 41 is generally wedge shaped in sagittal direction. This may facilitate positioning the pusher 41 and providing the force F in a desired direction. Further, a relatively thick dorsal side may reduce local pressure against the throat and may reduce or prevent possible associated discomfort or complications. The pusher 41 may be formed as a protrusion 41A formed on a base 41B (FIGS. 1B-1C), possibly of different materials and/or materials having different stiffness.

It is further noted that the relatively small thickness $T_V$ of the ventral side of the pusher 41 may reduce local pressure against the mandible and the soft tissue of the front part of the submental triangle and/or the chin, and thus possible associated discomfort and/or complications may be prevented. The combination of a V-shape and a relatively thick dorsal side assists providing an elevated pressure at the floor of the mouth, in particular at the submandibular triangles and possibly somewhat less so on the submental triangle, while reducing or preventing elevated pressure on the throat and airway.

To displace the soft tissue relative to (the angle and/or body of) the person's mandible 29, the pusher 41 should best be formed so as to fit at least partly inside the person's mandible 29, in particular fitting at least partly between the person's left and right angles, or: bodies, of the mandible 29, so as to deform in accordance with the shape and deformability of the person's floor of the mouth 15 and -mandible 29; see FIGS. 1B-1C. The protruding height $H_P$ of (the protrusion 41A of) the pusher 41 may vary from dorsal thickness $T_D$ to ventral thickness $T_V$, the variation preferably being continuously and smoothly and/or being in accordance with the deformability of the floor of the mouth 15 against the mandible 29 (which narrows from the angles towards the chin), so as to prevent excessive stress and/or pressure in the respective tissue portions. In particular, a width $W_P$ of a protrusion 41A of the pusher 41 may be equal to or smaller than a width $W_M$ of the space between the left and right body portions of the mandible 29 (see FIGS. 1B-1C), whereas a total with $W_b$ of (the base 41B) of the pusher 41 may be larger, even larger than a width of the mandible 29 (see FIGS. 1B-1C).

Thus, the pusher 41 is configured such that the mandible 29 does not hinder, restrict or prevent a desired displacement of the soft tissue of the floor of the mouth 15 relative to the mandible 29 due to the hardness of the mandible bone. Note that a simple strap 45 pulled across the floor of the mouth 15 but without a pusher 41 does not allow to push the tissue of the floor of the mouth 15 into the space between the left and right angles and/or bodies of the mandible 29, at least not to sufficient degree and direction to seal off, or at least to effectively seal off, the person's airway and prevent air leaks as discussed above. The protrusion height $H_P$ may preferably be about 0.5 cm and/or such that the floor of the mouth 15 may be pressed inward/upward for a distance $D_F$ of about 0.3-0.7 cm, e.g. about 0.4-0.6 cm such as about 0.5 cm, beyond the jaw tissue 13 surrounding the angle and/or body of the mandible 29 (see FIG. 1C).

Note further that the pusher may occupy a small volume below the floor of the mouth. The size of the pusher 41, in particular the protruding height $H_P$ and/or dorsal thickness $T_D$ of a wedge-shaped pusher may be chosen such that the assembly, in use, is arranged above (cranial to) the subject's thyroid, e.g. see FIGS. 1A, 3, 6-8.

At least part of the pusher 41 may be provided deformable pre-use and/or intra-use. Thus, at least part of the pusher 41 may be shaped to fit the anatomy of the person to be treated accurately. E.g., a pre-use deformable pusher may comprise a portion for shaping the pusher prior to application, e.g. having a malleable and/or plastically deformable portion. Embodiments may comprise one or more of a metallic and/or plastic support structure (e.g. one or more baleens), an amount of wax or putty and an inflatable or fluid-fillable portion, e.g. a bladder with an air or water input and a closure and/or valve. An intra-use deformable pusher may comprise a, possibly resilient, deformable portion that is deformable in situ on application in response to the person's anatomy and/or properties of the harness. Embodiments may comprise one or more of a metallic and/or plastic support structure (e.g. one or more baleens), an amount of soft wax or putty, an inflated and/or fluid-filled portion like a balloon, a gel pad, and a cushioning portion such as a foam pad or another spongy material. The latter may be preferred for ease of manufacturing and/or use and/or adaptability.

A cushioning pusher may be spongiform and/or it may have a thickness at rest Tr, over-all or at the dorsal side such that $Tr=T_D$ (at rest), of about 0.5-3 cm, e.g. 1.5-2 cm, and be reversibly compressible to a thickness Tc less than half that thickness Tr at a pressure against the floor of the mouth of about 0.1-0.3 kPa, like ca 0.2 kPa (about 2 cm $H_2O/cm^2$ in practical hospital units), preferably to about Tc<0.25 Tr at such pressures (a compression force of about 20 N/cm 2 or less per cm compression). A pusher with such compressibility values tends to be easily compressed against the floor of the mouth to adapt to the person's anatomy and to press the soft tissue of the floor of the mouth inward and against the laryngeal mask with a pressure of about 0.1-0.2 kPa. 0.2 kPa pressure on tissue is generally considered a safe pressure to prevent tissue damage, also in case of prolonged exposure. Further, such values allow that at least part of the pusher is located at or near the mandible and be compressed generally against the jaw (here meaning: tissue covered mandible) yet provide sufficient resiliency (or: resistance) to provide a suitable pressure force against the floor of the mouth as explained above. This facilitates positioning the pusher and/or increases applicability of the assembly to different anatomic varieties. The cushioning material may be provided over a portion of another material, e.g. a gel pad or a solid object. The normal capillary pressure in blood vessels ranges from about 16 to about 33 mm Hg in different segments. An external pressure of more than 33 mm Hg (this is equivalent to 4.3 kPa which again is equivalent to 0.43 N/cm$^2$) may occlude blood vessels so that underlying and surrounding tissues become anoxic; if such pressure continues for a critical duration, cell death may occur, resulting in soft tissue necrosis and/or eventual ulceration.

If a deformable and/or cushioning pusher just "leans" against the floor of the mouth, e.g. such that it is not pressed against the tissue and/or deformed by the mandible/due to the mandible, such pusher may not comprise a protrusion per se. However once the pusher is held by or attached to the harness and the pusher is pushed from exterior, by the harness, against the lower jaw and the floor of the mouth of the person, the pusher will deform by the mandible/due to the mandible, i.e. at the position of hard tissue of the floor of the mouth, locally more than at the soft tissue of the floor of the mouth. Thus, this may result in a shape as shown in FIG. 1C, wherein a relative thickening (or rather: less compression) of the pusher occurs at the location of the soft tissue thereby forming the protrusion height $H_P$ for urging the soft tissue in the cranial direction, as discussed herein.

Note that in some embodiments (e.g. see FIGS. 4, 7-8, 11A-12C) the protrusion may have or form a protrusion profile with, preferably in lateral direction, local elevated portions and a local recessed portion in between. This may provide the desired local elevated force at least predominantly to each of the submandibular triangles of the trigonum cervicale anterius while accommodating in the recessed portion at least part of the subject's throat for reducing or preventing, at least in comparison, such elevated force on the subject's throat (in particular at the submental triangle). Such shape may be provided by the "legs" of a V- or chevron-shape (e.g. FIG. 4), or by a pusher having a varying thickness in particular when having a kidney shape (e.g. FIGS. 7-8, 11A-12C). In some other embodiments (not shown) the pusher may be provided as an assembly comprising plural pusher elements adjacent each other which may facilitate providing adjustment for a subject's anatomic shape and/or medical apparel for (e.g. attached to) the subject.

The pusher 41 may be provided as a separate part which may be positioned against the person P and kept in place by the harness 39, but preferably the pusher 41 is attached to the harness 39. In such case, the pusher will generally form a protrusion on the inferior portion toward the superior portion of the harness. In particular, in case of a cushioning pusher, the pusher may be integrated in the harness wherein e.g. a band of the inferior portion (cf. band 45 in FIGS. 2-4) is provided as a suitably resiliently padded band over at least a portion of its length. In an embodiment, see FIG. 5, such padding may be formed as a soft sleeve 41 around a flexible member 45 of the harness.

A head-wearable harness 39 and an optional separate pusher 41 are shown, as explained below, in various views in FIGS. 6-12C, individually and, respectively, combined as an assembly.

Figure 6:
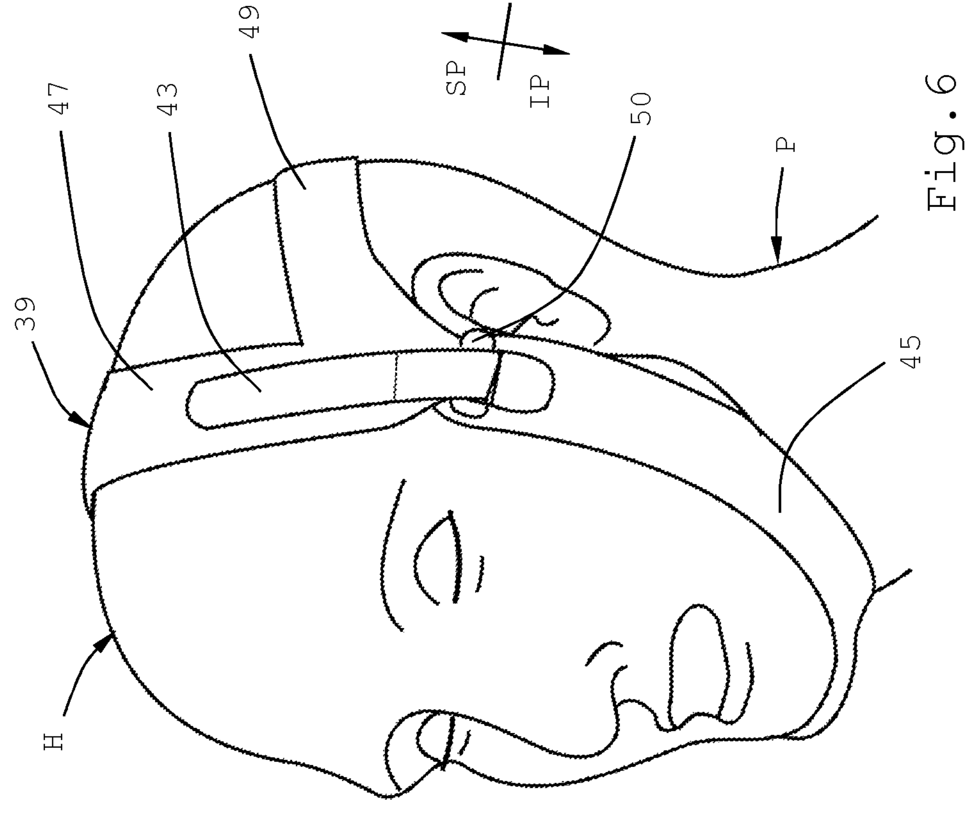
FIG. 6 is a side view of a person wearing a head wearable harness as disclosed herein.
Figure 9A:
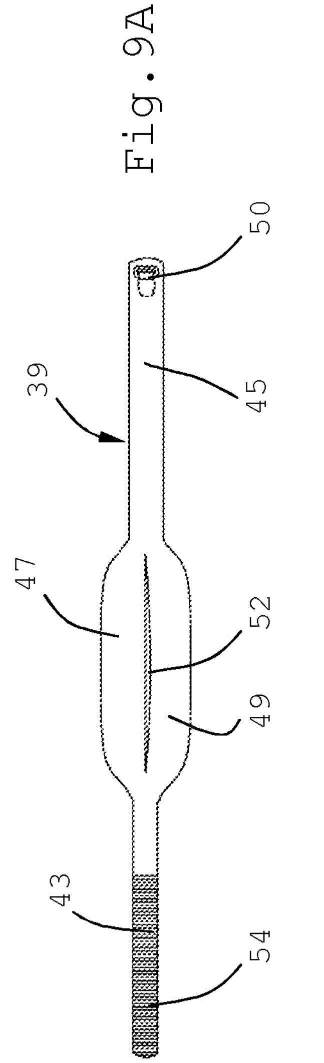
FIGS. 9A-9B are a top view and a bottom view, respectively, of the harness of FIGS. 6-8.
Figure 9B:
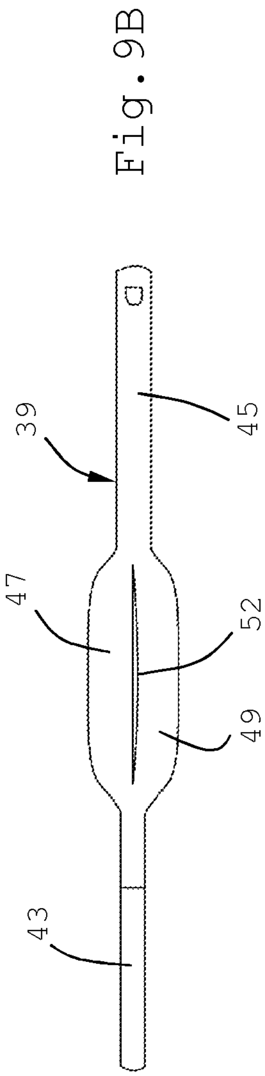

FIG. 6 shows the harness 39 per se arranged on a person's head H, FIGS. 9A-9B show the harness 39 lying flat. FIGS. 7-8 show the harness 39 in combination with a pusher 41.

The harness 39 per se may provide support for a pusher 41 (FIGS. 7-8) but may also, or in addition, be used for supporting and in particular fixing to the head H one or more other objects, e.g. tubes, wires, sensors, etc. optionally provided as separate parts. The harness 39 is head-wearable, i.e. arrangeable to be worn on a person's head H without external assistance and/or -support, to support the objects on the head H. This allows for the reliable positioning of the objects relative to the person's head H, independent of the position and/or the movement of the person's head. As an exemplary object, a pusher 41 can be attached to the harness 39 to be pressed against the person's head H and in particular against the floor of the person's mouth.

The harness 39 may comprise, as shown, one or more flexible members in the form of band sections 43, 45, 47, 49, several of which, e.g. 45, 47 and 49, may be formed as integral continuations of each other, possibly being unitary as shown (FIGS. 6-9B).

Band sections 47 and 49 may form one, preferably relatively broadened, band portion B which is provided with a slit 52 or on or more other suitable openings. The slit 52 and the flexibility of the band sections 47, 49 allow for the arrangement on a person's head of the band portion B as two band sections 47 and 49.

As before, one or more band sections 45, 47, are arranged, in use, encircling a person's head H generally in a direction parallel to the anatomic coronal plane (45, 47) and another band section 49 is arranged encircling the rear of the person's head H generally parallel to an anatomic transversal plane, keeping the former band sections 45, 47, in place. The head is left uncovered by the harness 39 frontal of the band sections 45, 47 so that the face and forehead are unobstructed, e.g. for access by care givers and/or devices such as bandages, electrodes, scanners etc. as well as not obstructing facial movement.

The harness 39 further comprises a ring 50 or another opening and/or a hook such that a belt portion 43 can be fed through the opening of the ring 50 and folded back to be formed as a looping-back portion for being be attached to itself or to another belt portion 47 of the harness 39 to form a closed loop of (bands 45, 47 of) the harness 39. Such a looping-back portion 43 may be provided on one side, as shown, but may also be provided on the opposite side or both sides of the harness (not shown). In the latter case, belt section 45 may be separable from the rest of the harness 39. Also or alternatively, any other suitable fastener as, for example, an adjustable buckle may be provided. Closing and/or opening the harness 39 on one or both sides facilitates donning the harness 39, also in case of existing connections between the person and further apparel (intubation tubes, monitoring electrodes etc.). A looping-back portion or adjustment portion oriented in inferior direction facilitates donning the harness and size adjustment and/or tightening it as substantially separate actions, possibly being performed single-handed and wherein tightening may primarily affect the inferior portion whereas the superior portion remains in place and forms an anchor, as it were, for the tightening.

FIGS. 7-8 further shows the harness 39 supporting a pusher 41 which is reversibly attached to the harness 39 per se by means of a further band 51 (cf. FIGS. 9A-9B; see also FIGS. 10A-12B). The further band 51 may be connected with one or more hook-and-loop-type fasteners on one or two sides and/or any other suitable fastener, for example, an adjustable buckle.

Different from the embodiments of FIGS. 1-5 the pusher 41 is sandwiched between the further band 51 and the harness 39. In another option (not shown) the harness 39 may be provided with an opening for the pusher 41 to extend through and to contact the person's skin. The pusher 41 may be attached prior to the harness 39 being arranged on a person's head H or, preferably, it may be arranged afterwards. In the latter case, the position and the pressing force of the pusher 41 against the floor of the mouth can be adjusted without manipulation of the harness 39. By arranging the harness 39 on a person's head H first and then arranging the pusher 41, the pusher 41 can be pressed against the floor of the mouth by pulling the ends of the further band 51 towards the superior portion SP and then (re-)attaching the further band 51 to the harness 39.

The shown pusher 41 has a generally transverse symmetric kidney-shape but other shapes may be used as well. The pusher 41 may be permanently attached to the further band 51 but it may also be provided as separate parts as shown in FIGS. 10A-12B, optionally attached (releasable or not) for use. The attachment may involve a hook and loop type fastener and/or any other suitable fastening method. Provision of the pusher 41 and further band 51 as separate parts facilitates manufacturing and it may facilitate independent selection and/or exchange of either.

Similar to the pusher 41, other objects, e.g. tube fixation straps, monitoring cables etc., may be attached to, and fixed by, the harness 39. For that, the harness 39 may be provided with one or more further connectors and/or hook-and-loop-type fastener portions (not shown); in particular one or more loop-type fabric portions for Velcro-style connections. Also in such cases, the separation between first donning the harness 39 and second attaching and/or adjusting the object (s) facilitates use and comfort of the person wearing the harness.

The disclosure is not restricted to the above described embodiments which can be varied in a number of ways within the scope of the claims. For instance the pusher and/or the harness may be shaped differently. Relative sizes of portions of the assembly may differ. The harness and/or pusher may be associated and/or connected with other devices; e.g. the harness and/or pusher may support one or more sensors attached to an/or embedded in the harness and/or pusher, respectively.

Elements and aspects discussed for or in relation with a particular embodiment may be suitably combined with elements and aspects of other embodiments, unless explicitly stated otherwise.

The invention claimed is:

1. A ventilation assembly for use in ventilation of a subject using a laryngeal mask, the assembly comprising a head-wearable harness and a pusher, wherein the harness is wearable on the subject's head for supporting the pusher to press against a floor of a mouth of the subject, wherein the pusher comprises local elevated portions for providing a pressure in a cranial direction and a recessed portion in between the elevated portions for accommodating a portion of a throat of the subject;

wherein the pusher is arranged, in use and operably supported by the harness on the subject, so that said elevated portions provide said pressure in the cranial direction between lateral sides of a mandible of the subject to soft tissue of the floor of the mouth of the subject and to displace said soft tissue of the floor of the mouth in the cranial direction relative to the mandible of the subject for urging internal soft tissue of the subject against the laryngeal mask in an airway of the subject as a seal to the mask when the laryngeal mask is installed in the airway of the subject.

2. The ventilation assembly according to claim 1, wherein the harness has a superior portion and an inferior portion, the superior portion is arrangeable on the subject's head and the inferior portion is arranged to support the pusher, and the pusher comprises a protrusion towards the superior portion for displacing the soft tissue and/or is configured to form a protrusion towards the superior portion to displace the soft tissue.

3. The ventilation assembly according to claim 2, wherein the superior portion comprises a piece of headwear and/or one or more flexible members operably connected or connectable to the inferior portion.

4. The ventilation assembly according to claim 2, wherein at least part of the inferior portion is elastic and at least part of the superior portion is substantially non-elastic.

5. The ventilation assembly according to claim 4, wherein the inferior portion comprises one or more flexible members being arrangeable under the subject's lower jaw and having an elastic portion, and the superior portion comprises one or more flexible members being arrangeable superior of the subject's ears and being substantially non-elastic.

6. The ventilation assembly according to claim 5, wherein the one or more flexible members of the inferior portion and the one or more flexible members of the superior portion are bands.

7. The ventilation assembly according to claim 2, wherein one of the superior portion and the inferior portion of the harness comprises an opening and/or a hook, and the other one of the superior portion and the inferior portion of the harness comprises a flexible member provided with a looping-back portion, the looping-back portion is formable or forms a loop through the opening and/or the hook, and the looping-back portion is attachable or attached to itself to close the loop for at least locally fastening the superior portion and inferior portion together.

8. The ventilation assembly according to claim 1, wherein at least one of a size, a shape, a position and an orientation of at least part of the pusher is adjustable.

9. The ventilation assembly according to claim 1, wherein the pusher comprises an inflatable portion and/or wherein the pusher is at least partly resilient.

10. The ventilation assembly according to claim 1, comprising mated connectors for attaching and/or detaching at least part of the pusher to the harness.

11. The ventilation assembly according to claim 1, wherein the pusher is wedge shaped in a cross section in a sagittal plane, and/or the pusher is V-shaped or chevron-shaped or kidney-shaped for, in situ under a subject's lower jaw, accommodating part of the subject's throat.

12. The ventilation assembly according to claim 1, wherein a superior portion of the flexible member is arrangeable on a head of the subject superior of the ears, and an inferior portion of the flexible member is arrangeable under a lower jaw of the subject.

13. The ventilation assembly according to claim 1, wherein the harness comprises at least one portion for size adjustment of the harness.

14. The ventilation assembly according to claim 1, wherein the harness has a superior portion and an inferior portion, the superior portion is arrangeable on a subject's head superior to the ears of the subject, and the inferior portion comprises one or more flexible members arrangeable under the subject's lower jaw, the harness comprises a flexible member configured to partially or fully encircle the subject's head generally parallel to an anatomic coronal plane and the harness is configured to leave, in use, the front portion of the head uncovered by the harness.

15. The ventilation assembly of claim 14 further comprising a selection of different sized and/or shaped pushers and/or pusher inserts.

16. An assembly comprising the ventilation assembly according to claim 1 and a laryngeal mask.

17. The assembly of claim 16 further comprising a selection of different sized and/or shaped pushers and/or pusher inserts.

18. A method of ventilating a subject comprising:

operably installing a laryngeal mask in an airway of the subject, and urging internal soft tissue of the floor of the mouth of the subject against the laryngeal mask in the airway of the subject for at least partly sealing the airway and preventing leaks along the laryngeal mask using a pusher comprising local elevated portions for providing a pressure in a cranial direction between lateral sides of a mandible of the subject to the soft tissue of the floor of the mouth of the subject, and a recessed portion in between the elevated portions for accommodating a portion of a throat of the subject to urge the soft tissue of the floor of the mouth of the subject in a cranial direction of the subject relative to the mandible of the subject.

19. The method of claim 18, comprising:

providing the subject with a ventilation assembly comprising: a head-wearable harness and a pusher, wherein the harness is wearable on the subject's head for supporting the pusher to press against the floor of the mouth of the subject, wherein the pusher is arranged, in use and operably supported by the harness on the subject, to provide the local elevated pressure in a cranial direction between the lateral sides of the mandible of the subject to the soft tissue of the floor of the mouth of the subject and to displace the soft tissue of the floor of the mouth in the cranial direction relative to the mandible of the subject for urging the internal soft tissue of the subject against the laryngeal mask in the airway of the subject as a seal to the mask when the laryngeal mask is installed in the airway of the subject, and arranging the pusher to displace the soft tissue of the floor of the mouth of the subject in cranial direction of the subject.

20. The method of claim 19, comprising deforming the pusher in accordance with at least one anatomic characteristic of the subject.

* * * * *